United States Patent [19]
Yoshida et al.

[11] Patent Number: 4,892,935
[45] Date of Patent: Jan. 9, 1990

[54] ANTI-HUMAN PULMONARY CARCINOMA MONOCLONAL ANTIBODY

[75] Inventors: Hajime Yoshida, Sagamihara, Japan; Nobuo Hanai, Mercer Island, Wash.; Kenya Shitara, Machida, Japan

[73] Assignee: Kyowa Hakko Kogyo Co., Ltd., Tokyo, Japan

[21] Appl. No.: 70,052

[22] Filed: Jul. 6, 1987

[30] Foreign Application Priority Data

Jul. 11, 1986 [JP] Japan ................................. 61-163415

[51] Int. Cl.$^4$ ..................... A61K 39/395; C07K 16/14
[52] U.S. Cl. .................... 530/387; 530/395; 530/806; 530/808; 530/828; 435/192.2; 435/240.27; 424/85.8
[58] Field of Search ............... 530/387, 806, 828, 395; 435/240.27

[56] References Cited

U.S. PATENT DOCUMENTS

| | | | |
|---|---|---|---|
| 4,569,788 | 2/1986 | Mulshine et al. | 530/378 |
| 4,683,200 | 7/1987 | Hirohashi et al. | 530/378 |
| 4,737,579 | 4/1988 | Hellström et al. | 530/387 |

OTHER PUBLICATIONS

Fernsten et al., Cancer Res., 46, 2970–2977, Jun. 1986.
Pettijohn et al., Cancer Res., 47, 1161–1169, Feb., 1987.
Endo et al., Cancer Res., 46, 6369–6373, Dec. 1986.
Watanabe et al., Cancer Res., 47, 826–829, Feb. 1987.
Cancer Res., vol. 42 (1982) 150:4.
Cancer Res., vol. 42 (1982) 3187:92.
Cancer Res., vol. 45 (1985) 3274:81.
Cancer Res., vol. 46 (1986) 4438:43.
Cancer Res., vol. 47 (1987) 1267:72.
J. Surg. Res., vol. 30 (1981) 403:8.
J. Immun., vol. 131, No. 1 (1983) 497:502.
Transp. Proc., vol. XIII, No. 4 (1981) 1942:6.

Primary Examiner—Margaret Moskowitz
Assistant Examiner—Jeff Kushan
Attorney, Agent, or Firm—Fitzpatrick, Cella, Harper & Scinto

[57] ABSTRACT

Monoclonal antibodies being capable of reacting with human squamous cell lung carcinoma, lung adenocarcinoma and large cell lung carcinoma, and non-reactive with human small cell lung carcinoma and normal human lung cells, and recognizing glycoproteins as antigens. Hybridomas having the characteristics of cell line SLC-454 secrete such antibodies. Method of diagnosing human lung cancer and method of therapeutic treatment are described.

3 Claims, 3 Drawing Sheets

ANTI-HUMAN PULMONARY CARCINOMA MONOCLONAL ANTIBODY

BACKGROUND OF THE INVENTION

The present invention relates to an anti-human pulmonary carcinoma monoclonal antibody, which is capable of highly frequent reaction with three tissue types of human pulmonary carcinoma, i.e. squamous cell carcinoma, adenocarcinoma and large cell carcinoma, and is non-reactive with human small cell carcinoma and normal human lung cells. The antibody recognizes glycoproteins as the antigen and belongs to the class IgM.

Since the monoclonal antibody according to the present invention is capable of effectively detecting lung cancer except for small cell lung carcinoma, it is useful for the pathologic and serologic diagnosis of lung cancer.

Monoclonal antibodies which are capable of specifically reacting with various human cancers as constructed by the technique of obtained hybridomas have recently been reported. While there are many reports on monoclonal antibodies capable of reacting with human lung cancer [Cancer Res., 42, 150 (1982); Cancer Res., 42, 3187 (1982); J. Surgical Res., 30, 403 (1981); Transplantation Proceed , XIII (4), 1942 (1981); J. Immunol., 131 (1), 497 (1983); Abstracts of Papers, Japan Society of Immunology, P. 212 (Abstract No. 107) (1983); J. Immunol., 131 (1), 497 (1983); Cancer Res., 46, 4438 (1986); Cancer Res., 47, 1267 (1987)], no monoclonal antibodies being capable of equally reacting three tissue types of human lung cancer, i.e. squamous cell carcinoma, adenocarcinoma and large cell carcinoma but non-reactive with small cell carcinoma cells have been known.

Carcinoembrionic antigen (CEA), known as tumor marker, is present not only in all pulmonary carcinoma tissue types, but also in normal lung tissue and serum, and is so, not specific to lung cancer. Thus, the positive rate to lung cancer is not very high with CEA.

The remedy and prognosis of small cell lung carcinoma among four types of pulmonary carcinoma are quite different from those of the other three types. Accordingly, a monoclonal antibody which can distinguish squamous cell carcinoma, adenocarcinoma and large cell carcinoma from small cell carcinoma, if available, would be useful in the diagnosis of lung cancer.

The present inventors have found that monoclonal antibodies produced by hybridomas between spleen cells of a mouse immunized with membrane fractions of human squamous cell lung carcinoma and murine myeloma cells have good reactivity with not only squamous cell lung carcinoma to be used as the immunogen but also to lung adenocarcinoma and large cell lung carcinoma and so are applicable in pathologic, serologic and pleural effusional diagnosis.

SUMMARY OF THE INVENTION

The present invention provides an anti-human pulmonary carcinoma monoclonal antibody which is capable of, with high frequency, reacting with human squamous cell lung carcinoma, lung adenocarcinoma and large cell lung carcinoma, and is non-reactive with human small cell lung carcinoma and normal human lung cells. The antibody recognizes glycoproteins as the antigen and belongs to the class IgM.

BRIEF DESCRIPTION OF THE DRAWINGS

In the accompanying drawings,

In FIG. 2, the symbols are used as follows: ○ for treatment with 0.1 U/ml neuraminidase, △ for treatment with 0.1 U/ml α-L-fucosidase, ■ for treatment with 0.25% trypsin, □ for treatment with 10 U/ml protrease, ● for treatment with 50 mM $NaIO_4$, and X for no treatment.

In FIG. 3, the symbols are used as follows: ▲ for SLC-454, ○ for rabbit anti-CEA antibody, ● for rabbit anti-AFP antibody, and △ for rabbit anti-$β_2$ microglobulin antibody.

DESCRIPTION OF THE INVENTION

The monoclonal antibody according to the present invention is obtained by rendering a mouse immunologically tolerant as a result of pretreatment with normal human lung cells, fusing spleen cells of the mouse immunized with membrane fractions of human squamous cell lung carcinoma and murine myeloma cells, selecting from among the hybridomas obtained, a hybridoma clone producing a monoclonal antibody having specificity to human pulmonary carcinoma, and cultivating the selected hybridoma in a medium or administering the hybridoma to a mouse to thereby cause hybridoma cell propagation in the ascitic fluid in the mouse, followed by separation from the culture or ascitic fluid.

As a typical example of the monoclonal antibodies according to the present invention, there may be mentioned SLC-454 produced by the hybridoma cell line SLC-454.

The hybridoma cell line SLC-454 has been deposited with the European Collection of Animal Cell Cultures, Great Britain, as of July 3, 1986 as ECACC No. 86070306 under the Budapest Treaty.

In the following, a method of producing the monoclonal antibodies according to the invention is described in detail.

(1) Immunization of animal and preparation of antobody-providing cells

Mice between 3–10 weeks of age, preferably 8-week-old mice, are immunized with human squamous cell lung carcinoma cells, tissues or membrane fraction to such mice to prepare antibody-producing cells in the spleen, lymph node and peripheral blood. Mice rendered immunologically tolerant as a result of pretreatment with normal human lung cells are preferably used as the mice to be immunized. The immunization is performed generally by administering human squamous cell lung carcinoma cells ($10^6$ to $10^7$ cells per animal), human squamous cell lung carcinoma tissues, or membrane fractions (membrane fragments) derived from such tissues (10–500 μg per animal) together with an appropriate adjuvant (e.g. Freund's complete adjuvant, or aluminum hydroxide gel plus B. pertussis vaccine) administered to the animals subcutaneously, intravenously or intraperitoneally. Thereafter, the antigen administration is repeated 2-5 times at 1- to 2-week intervals without an adjuvant. Three to seven days after each immunization, the blood is sampled from the eyeground venous plexus and the serum of each sample is tested to determine whether it reacts with human pulmonary squamous cell carcinoma by the enzyme immunoassay technique given below [Enzyme-linked Immunosorbent Assay (ELISA), published by Igaku Shoin, Tokyo 1976], for instance.

Normal human and tumor tissues are obtained from autopsies or surgical operations. The tissues are immediately frozen and stored at $-80°$ C. For membrane components the tissues are thawed at $4°$ C. in PBS containing 1 mM phenylmethyl sulfonyl fluoride. After mincing they are disrupted with an ultra disperser (LK-21; Yamato, Tokyo, Japan) and homogenized with a teflon-glass homogenizer. The homogenate is centrifuged at $100,000 \times g$, and then the pellet is resuspended at 1 mg protein in 1 ml of PBS and stored at $-80°$ C.

Enzyme immunoassay technique:

The membrane preparations of normal or tumor cells or tissues (membrane fragment fraction containing 10-1,000 $\mu g$ of proteins per ml) are distributed into wells of a 96-well plate for EIA (product of Flow Laboratories) (100-200 $\mu l$ per well). After allowing the membrane preparations to stand overnight to two overnights at $4°$ C., the supernatant is removed from each well, and each well is washed well with deionized water or phosphate-buffered saline (PBS; 1.83 g of disodium phosphate, 0.21 g of monopotassium phosphate and 7.65 g of sodium chloride in each liter of distilled water, pH 7.2). Then, 1% BSA (bovine serum albumin)-PBS is distributed into the wells (100-200 $\mu l$ per well) and protein-binding sites remaining on the plate are blocked by allowing the culture to stand overnight to two overnights at $4°$ C. After discarding the BSA-PBS, the wells are washed well with deionized water or PBS. Samples (mouse sera, hybridoma culture supernatants, or roughly purified monoclonal antibodies; each as the first antibody) are diluted with BSA-PBS and the dilutions are distributed into the wells (100 $\mu l$ per well), followed by overnight standing at $4°$ C. After washing the wells once with deionized water and then 6 times with 2 M NaCl solution, a 100-fold dilution of the rabbit anti-mouse immunoglobulin IgG-peroxidase conjugate (produced by DAKO and distributed by Kyowa Medex; used as the second antibody) is distributed into the wells (100 $\mu l$ per well). The plate is then allowed to stand at room temperature for 2 hours.

After washing well with PBS, an ABTS substrate solution [prepared by dissolving 550 mg of 2,2'-azinobis (3-ethylbenzothiazoline-6-sulfonic acid) diammonium salt in 1 liter of 0.1 M citrate buffer (pH 4.2) and adding, just prior to use, hydrogen peroxide to a concentration of 1 $\mu l/ml$] is applied and the color developed is measured in terms of the absorbance $OD_{415nm}$. Those mice that strongly react with the squamous cell lung carcinoma cells, tissues or membrane preparations are used as human squamous cell lung carcinoma-immunized mice, namely as sources of supply of antibody-producing cells for the hybridoma production.

When cells as such are used as the antigen in performing enzyme immunoassay, the target cells are cultivated on a Falcon 3072 plate, 0.25% glutaraldehyde-PBS is added and, after allowing it to stand at room temperature for 1-2 hours, the plate is washed well with PBS. Then, 100-200 $\mu l$ of 1% BSA-PBS is added and, after 2 hours of standing, the plate is washed well with deionized water or PBS and submitted to antibody titer determination, which is conducted in the same manner as the case where an ordinary antigen-coated plate is used.

For submitting to cell fusion, human squamous cell lung carcinoma cells, tissues or membrane preparations are intraperitoneally administered to the immunized mice in a dose of 2 to $5 \times 10^6$ cells per animal or 20 to 400 $\mu g$ per animal 3-4 days prior to the fusion treatment. The spleen is extirpated, cut into fragments in MEM (product of Nissui Pharmaceutical), loosened up with a pair of forceps, and centrifuged at 1,200 rpm for 5 minutes. The supernatant is discarded, and the cells obtained as the sediment are deprived of erythrocytes by treatment with Tris-ammonium chloride buffer (pH 7.65) for 1-2 minutes, washed three times with MEM, and used as the spleen cells for fusion.

(2) Preparation of myeloma cells

A mouse-derived established myeloma cell line is used. Usable examples of such cell line include the 8-azaguanine resistant mouse (BALB/c-derived) myeloma cell lines P3-X63Ag8-U1(P3-U1) [Current Topics in Microbiology and Immunology-1] P3-NSI/1-Ag4.1 (NS-1) [European J. Immunology, 6, 511–519 (1976)], SP2/0-Ag14 (SP-2) [Nature, 276, 269–270 (1978)], P3-X63-Ag8 653 (653) [J. Immunology, 123, 1548–1550 (1979)] and P3-X63-Ag8 (X63) [Nature, 256, 495–497 (1975)]. The passage of these cell lines is performed in 8-azaguanine medium [normal medium prepared by adding, to RPMI-1640 medium, glutamine (1.5 mM), 2-mercaptoethanol ($5 \times 10^{-5}$ M), gentamycin (10 $\mu g/ml$) and fetal calf serum (FCS; produced by CSL) (10%), with further supplementation with 8-azaguanine (15 $\mu g/ml$)]. The cell line for cell fusion should be transferred to normal medium 3-4 days before fusion to ensure the cell count of not less than $2 \times 10^7$ on the time of cell fusion.

(3) Cell fusion

The splenocytes immunized in (1) and the myeloma cells obtained in (2) are washed well with MEM or PBS and mixed in a cell number ratio of splenocytes: myeloma cells=5 to 10:1 and then the mixture is subjected to centrifugation (1,200 rpm, 5 minutes). The supernatant is discarded and the cell sediment is loosened up. With stirring at $37°$ C., a mixture of 2 g of polyethylene glycol 1000 (PEG-1000), 2 ml of MEM and 0.7 ml of dimethyl sulfoxide is added in an amount of 0.2-1 ml per $10^3$ splenocytes, and after several additions of 1-2 ml of MEM at 1- to 2-minute intervals, MEM is added until the whole volume is made 50 ml. After centrifugation (900 rpm, 5 minutes), the supernatant is discarded and the cell sediment is loosened gently. To the cells is added 100 ml of normal medium (RPMI-1640 with 10% FCS). The cells are suspended in the medium by gentle drawing up into the discharging from a measuring pipette.

The suspension obtained is distributed, in 1 ml-portions, into the wells of a 24-well incubation plate. Incubation is carried out in a 5% $CO_2$ incubator at $37°$ C. for 24 hours. HAT medium [normal medium supplemented with hypoxanthine ($10^{-4}$ M), thymidine ($1.5 \times 10^{-5}$ M) and aminopterine ($4 \times 10^{-7}$ M)] is added to the incubation plate (1 ml per well) and incubation is conducted for a further 24 hours. Thereafter, 1 ml of the culture supernatant is discarded and the same volume of fresh HAT medium is added at 24-hour intervals for 2 days.

The incubation in the $CO_2$ incubator at 37° C. is continued for 10–14 days.

For those wells in which fused cells grown and forming colonies are found, 1 ml of the supernatant is discarded and the same volume of HT medium (HAT medium minus aminopterine) is added, followed by medium replacement with fresh portions of HT medium at 24-hour intervals for 2 days.

After 3–4 days of cultivation in HT medium, a portion of the culture supernatant is collected and assayed for antibody titer relative to human pulmonary carcinoma by the above-mentioned enzyme immunoassay technique. Simultaneously, the reactivities with normal human cells or tissues and membrane preparations thereof, among others, are also determined by a similar method, and those wells for which selective reactivity with human pulmonary carcinoma cells or tissues or membrane preparations thereof is observed are selected. For the wells showing strong reactivity with human pulmonary carcinoma cells or tissues or membrane preparations thereof but no reactivity with normal human cells or tissues or membrane preparations thereof, among others, cloning is repeated twice by the limiting dilution technique. In this way, those clones for which high antibody titer values are stably obtainable relative to human pulmonary carcinoma cells or tissues or membrane preparations thereof are selected as anti-human pulmonary carcinoma monoclonal antibody-producing hybridoma cell lines.

(4) Preparation of monoclonal antibodies

Eight- to ten-week-old female BALB/c nude mice treated with pristane [intraperitoneally administered with 0.5 ml of 2,6,10,14-tetramethylpentadecane (pristane) and fed for 1 to 2 weeks] are intraperitoneally injected with the anti-human pulmonary carcinoma monoclonal antibody-producing hybridoma cells obtained in procedure (3) above at a dose of 2–4 $\times 10^6$ cells per animal. Within 10–21 days, the hybridoma cells produce ascites carcinoma in the mice An ascitic fluid is collected from such mice, centrifuged (3,000 rpm, 5 minutes) to remove solids, subjected to salting out with 50% ammonium sulfate, dialyzed against phosphate buffer supplemented with NaCl (0.5 M), and passed through a Sephacryl S-300 (product of Pharmacia Fine Chemical) column (bed volume 750 ml) at a flow rate of 15 ml/hr. An IgM fraction is collected and used as a purified monoclonal antibody.

The isotype of the antibody is determined by Ouchterlony's method (double immunodiffusion) [Seibutsukagaku Jikkenho (Methods in Experimental Biochemistry), vol. 15, Introduction to Experimental Immunology, p. 74, Gakkai Shuppan Center, 1981].

The quantity of protein is estimated by the Folin's method, followed by calculation based on the absorbance at 280 nm [1.4 (OD280) approximately corresponds to 1 mg of immunoglobulin per ml].

The monoclonal antibodies thus obtained are evaluated for specificity characteristics based on the reactivities with (1) normal and tumor tissues and membrane fractions thereof derived from a variety of human organs obtained from a plurality of subjects, (2) the reactivities with a variety of normal human or tumor cell lines, or human fetal cell lines and membrane preparations derived therefrom, (3) the reactivity with the hitherto known carcinoembryonic antigen (for example, CEA) and (4) the reactivities with normal human-derived and patient-derived sera, and the like, as determined by an appropriate assay technique, such as the enzyme immunoassay method, fluorescent antibody method, immunohistological staining method (ABC method), etc. Those monoclonal antibodies that react only with human pulmonary carcinoma but do not exhibit reactivity in any of the above evaluation tests are selected.

The thus-obtained monoclonal antibodies which specifically react with human pulmonary carcinoma, are expected to be useful in diagnosis of lung cancer by serologic examination, histological examination, imaging, etc., or in the treatment of lung cancer which comprises administering the antibodies as they are or in the form of the so-called immunotoxins, namely conjugates with anticancer agents or toxins, to cancer patients It is further expected that these tumor-specific monoclonal antibodies might contribute, through the use of affinity columns in which they are used, to the purification of tumor-specific antigens, to the analysis of such antigens and further to the development of lung cancer vaccines.

(5) Immunohistochemical staining method (ABC method)

The following procedure is carried out according to the immuno-peroxidase method described below using a Vectastain ABC kit (product of Vector Laboratories, Burlingame, Calif.).

The formalin-fixed and paraffin-embedded tissue sections sliced to a thickness of 5 μm using microtome are mounted on slide glass coated with egg white albumin, dewaxed in xylene, and gradually hydrated through alcohols/water.

After washing with deionized water for 5 minutes, endogenous peroxidase is blocked by immersion in 0.3% (wt/vol) hydrogen peroxide in an absolute methanol at room temperature for 30 minutes. Sections are washed with a phosphate buffer for 20 minutes and incubated with diluted normal horse serum at room temperature for 20 minutes. An excessive serum is soaked up, and SLC-454 (20 μg/ml) is added as the first antibody. The glass is allowed to stand at room temperature for 30 minutes and then washed with PBS. A biotinylated antimouse immunoglobulin horse antibody is added to the sections and the glass is allowed to stand for 30 minutes and then washed with PBS.

Then, an avidin-biotin-peroxidase (ABC reagent) is added to the sections and the glass is allowed to stand for 30 minutes and then washed with PBS. Thereafter, the sections are incubated for 2 minutes in a peroxidase substrate solution (mixture of 0.02% hydrogen peroxide and 0.1% diaminobenzidine tetrahydrochloride in 0.1 M Tris-hydrochloride buffer, pH 7.2) and the reaction is stopped by putting the glass into ice-cold water The sections are counterstained with hematoxylin, dehydrated in alcohols/water and xylene and settled with canada balsam [Rinshokensa 28, 353 (1984)].

(6) Serum diagnosis of lung cancer

The serum diagnosis is performed as follows:

A first antibody preparation (10–100 μg/ml) is distributed into the wells of a 96-well plate for EIA (50–200 μl per well). The plate is allowed to stand at 4° C. overnight to two overnights or at room temperature for 2–4 hours. After washing with PBS, 200 μl of BSA-PBS is added to each well, followed by further standing at 4° C. overnight or at room temperature for 2 hours. The plate is then washed well with PBS, and 50–100 μl of a 1-to 100-fold dilution of a serum sample is added to each well. After allowing the plate to stand at 4° C. overnight or at room temperature for 2 hours, the plate is washed well with PBS. Then, a biotin- or peroxidase-labeled second antibody (10–100 μg/μl) is added to the wells (50–100 μl per well) and the plate is further allowed to stand at 4° C. overnight or at room temperature for 2–4 hours. When a biotin-labeled antibody is used as the second antibody, the plate is washed well with PBS, avidin-biotin-peroxidase (10 μg/ml) is added to the wells (50–100 μl per well), and the plate is allowed to stand at room temperature for 30 minutes and then washed well with PBS. Then, an ABTS substrate solution is added, as the substrate solution, in an amount of 50–100 μl per well. After allowing the plate to stand at room temperature for 10–30 minutes, the reaction is terminated by adding 5% SDS solution in an amount of 50–100 μl per well. The $OD_{415}$ value is measured for each well and the quantity of the antigen in the serum sample is calculated based on the intensity of the color developed. By comparing the antigen levels in the sera of healthy humans with those in the sera of patients with lung cancer, a normal level range is defined When the level in question exceeds such a predetermined range, the test for lung cancer is regarded as positive.

(7) Antigen analysis

In performing the above-mentioned enzyme immunoassay, immunohistochemical staining or serum diagnosis, the antigens (squamous cell lung carcinoma membrane preparations, cultured lung cancer cell lines, lung cancer tissues) are pretreated with reagents such as enzymes (e.g. neuraminidase, protease) and sodium periodate and then reacted with the monoclonal antibodies. The subsequent comparison for differences in reactivity with the monoclonal antibodies between the original antigens without such pretreatment and the antigens pretreated in the above manner can elucidate the chemical characteristics of the antigenic sites which the monoclonal antibodies recognize. That is, if the antigenicity disappears upon treatment with neuraminidase, it is assumed that sialic acids are associated with the antigenic determinants. If the antigenicity disappears upon treatment with protease, it is assumed that proteins are associated with the antigenic determinants. If the antigenicity disappears upon sodium periodate treatment, sugar chains are presumably associated with the antigenic determinants.

(8) Judgment whether SLC-454 is different from known cancer markers or not by competitive binding inhibition test Pulmonary carcinoma membrane preparations coated on a plate for EIA are blocked by 1% BSA solution, and serial-dilutions of SLC-454, rabbit anti-CEA antibody, rabbit anti-AFP antibody and rabbit anti-$\beta_2$-microglobulin antibody are added. After overnight standing at 4° C., the plate is washed well with PBS. Then, biotin-labeled SLC-454 is added and allowed to stand at room temperature for 3–4 hours. After washing, avidin-biotin-peroxidase (Vectastain ABC immunoperoxidase staining kit; product of Vector) is added and the plate is allowed to stand at room temperature for 1 hour. Then, an ABTS substrate solution is added and the absorption at 415 nm is measured for each well.

If the first antibody recognizes the same antigen (epitope) that SLC-454 recognizes, the binding site of biotin-labeled SLC-454 as the second antibody is occupied by the first antibody, and thus the second antibody is incapable of being bound to the antigen and the color development is inhibited. Accordingly, in the above method, if the binding of the second antibody (biotin-labeled SLC-454) is not inhibited by the first antibody, it is assumed that SLC-454 recognizes the different antigen from the first antibody.

The following examples illustrate the invention in further detail.

EXAMPLE 1

(1) Preparation of antibody-producing cells

Normal human pulmonary tissue membrane preparations were administered intravenously to new-born (BALB/c×C57BL/6)$F_1$ mice within 24 postnatal hours at a dose of 100 μg of proteins per animal. After the lapse of 8 weeks, the mice were intraperitoneally administered with human squamous cell lung carcinoma membrane preparations (100 μg of proteins per animal) together with aluminum hydroxide gel (2 mg per animal) and killed B. pertussis vaccine ($1 \times 10^9$ per animal), followed by 3–5 immunizations with the same antigen without an adjuvant at a dose of 100 μg per animal on the protein basis at 1- to 2-week intervals. From among these immunized mice, those mice whose antisera are intensely reacted with human pulmonary carcinoma cells or tissues or membrane preparations derived therefrom were selected as the immunized mice, and spleen cells were prepared from such mice and submitted to cell fusion.

(2) Preparation of myeloma cells

The 8-azaguanine-resistant mouse myeloma cell line P3-U1 was cultivated in normal medium to thereby secure not less than $2 \times 10^7$ cells at the time of cell fusion, and submitted to cell fusion as a parent strain.

(3) Hybridoma production

The spleen cells and myeloma cells obtained in (1) and (2), respectively, were used in a ratio of 5:1 and subjected to fusion following the procedure mentioned hereinabove. After cultivation in HAT medium at 37° C. under 5% $CO_2$ for 14 days, fused cells were selected in HAT medium and, after change of the medium to HT medium, cultivation was continued. Based on the results of anti-human pulmonary carcinoma antibody titer determination, active wells were selected and, after change of the medium to normal medium, cloning was repeated twice. The hybridoma cell line SLC-454 having no reactivity with normal human cells or tissues or other cancers but having specific reactivity with human pulmonary carcinoma, as determined by various assay methods, was thus selected.

(4) Monoclonal antibody purification

Pristane-treated 8-week-old female BALB/c nude mice were intraperitoneally injected with the hybridoma cell line SLC-454 obtained in (3) at a dose of $4 \times 10^6$ cells per animal. Within 10–21 days, the hybridoma produced ascites carcinoma. An ascitic fluid was collected from ascitic fluid-bearing mice (5–10 ml per animal), deprived of solids by centrifugation (3,000 rpm, 5 minutes), subjected to salting out with 50% ammonium sulfate, dialyzed against PBS supplemented with NaCl (0.5 M), and passed through a Sephacryl S-300 (product of Pharmacia Fine Chemicals) column (bed volume 750 ml) at a flow rate of 15 ml/hr. An IgM fraction was collected and used as purified antibody.

(5) Specificity of SLC-454

Reaction specificity of the thus-obtained anti-pulmonary carcinoma-specific monoclonal antibody SLC-454 are given in Table 1.

TABLE 1

| Target | | | Antibody SLC-454 The number of positive results to total test samples |
|---|---|---|---|
| Affinity analysis (ELISA) | Tissues membrane component | Squamous cell lung carcinoma | 3/12 |
| | | Lung adenocarcinoma | 2/10 |
| | | Large cell lung carcinoma | 1/3 |
| | | Normal lung | 0/6 |
| | | Normal tissues other than lung* | 0/11 |
| | Purified antigen | CEA | — |
| | Cultured cell lines | Squamous cell lung carcinoma | 1/2 |
| | | Lung adenocarcinoma | 2/2 |
| | | Large cell lung carcinoma | 1/1 |
| | | Small cell lung carcinoma | 0/2 |
| | | Fetal lung | 1/5 |
| | | Cancers other than lung cancer** | 2/5 |
| | | Normal lung cell | 0/1 |

*Stomach, liver, kidney, pancreas, gall bladder, heart, large intestine, small intestine
**One of two pancreatic cancer cell lines and one of three gastric cancer cell lines were stained.

EXAMPLE 2

Various cancer tissues were immunohistochemically stained using the monoclonal antibody SLC-454 obtained in Example 1. Thus, paraffin-embedded block sections derived from seven patients with squamous cell lung carcinoma, seven patients with lung adenocarcinoma, five patients with large cell lung carcinoma, three patients with small cell lung carcinoma, four patients with gastric cancer, three patients with hepatoma, one patient with pancreatic cancer, one patient with rectal cancer, one patient with leukemia, one patient with bile duct cancer, one patient with urinary bladder cancer, one patient with neuroblastoma, one patient with uterine cancer and one patient with palatine cancer were stained. And various normal adult and fetal tissues were also immunohistochemically stained. The results are shown in Table 2.

TABLE 2

| Tumor type | SLC-454 The number of positive results to total test samples |
|---|---|
| Squamous cell lung carcinoma | 7/7 |
| Lung adenocarcinoma | 6/7 |
| Large cell lung carcinoma | 4/5 |
| Small cell lung carcinoma | 0/3 |
| Gastric cancer | 2/4 |
| Hepatoma | 0/1 |
| Pancreatic cancer | 1/1 |
| Rectal cancer | 0/1 |
| Leukemia | 0/1 |
| Bile duct cancer | 1/1 |
| Bladder cancer | 0/1 |
| Neuroblastoma | 0/1 |
| Uterine cancer | 1/1 |

TABLE 2-continued

| Tumor type | SLC-454 The number of positive results to total test samples |
|---|---|
| Palatine cancer | 0/1 |

And normal adult and fetal tissues (lung, spleen, stomach, large intestine, small intestine, heart, liver, kidney, bone marrow, thyroid gland, brain, pancreas) gave negative results.

EXAMPLE 3

Figure 1:
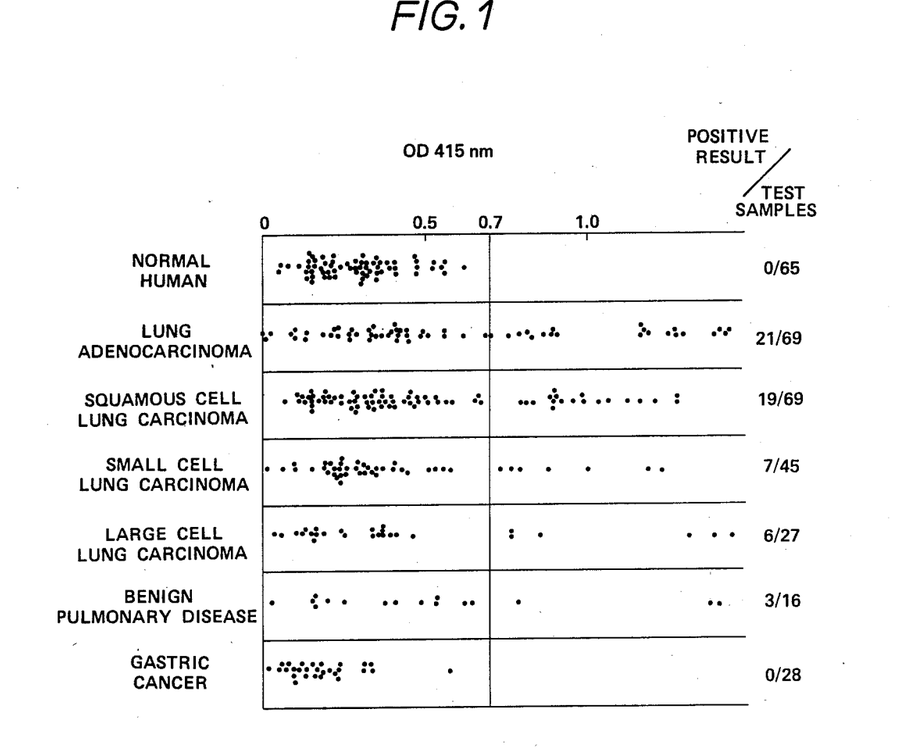
FIG. 1 is a scatter chart showing the results of serum diagnosis of pulmonary carcinoma using the monoclonal antibody SLC-454.

A suspension of SLC-454 (10 μg/ml) was distributed in 50 μl-portions into the wells of a 96-well plate for EIA (product of Flow Laboratories). After allowing it to stand overnight at 4° C., the plate was washed with PBS. Then, 1% BSA-PBS was added (200 μl per well). After overnight standing, the plate was washed well with PBS. To the plate were added 20-fold dilutions of normal human-derived sera (65 samples) or of lung cancer patient-derived sera (210 samples) in an amount of 100 μl per well. After overnight standing at 4° C., the plate was washed well with PBS. Then, biotin-labeled anti-lung cancer monoclonal antibody SLC-454 (5 μg/ml) was added as the second antibody (100 μl per well). The plate was allowed to stand overnight at 4° C. and, then, washed well with PBS. Avidin-biotin-peroxidase (product of Vector) (10 μg/ml) was distributed in 100 μl-portions into the wells, and the plate was allowed to stand at room temperature for 1 hour and then washed with PBS. Thereafter, an ABTS substrate solution was added in an amount of 100 ul per well and the reaction was allowed to proceed at room temperature for 30 minutes and then terminated by adding 5% SDS (sodium dodecyl sulfate) solution (100 μl per well). For each well, the color development was measured using an absorptiometer ($OD_{415}$) As shown in FIG. 1, no positive result ($OD_{415}$>0.70) was given for 65 serum samples from healthy subjects, whereas; for the serum samples from lung adenocarcinoma patients, 21 out of 69 samples; for the serum samples from squamous cell lung cancer patients, 19 out of 69; for serum samples from large cell lung carcinoma patients, 6 out of 27 samples gave positive results. However, for the serum samples from small cell carcinoma lung patients, 7 out of 45 samples gave positive results in the above serum diagnosis system. For the serum samples from benign pulmonary diseases patients, 3 out of 16 samples gave positive results; and, for the serum samples from gastric cancer patients, none of 28 cases. These results show that the serum diagnosis using SLC-454 is effective in lung cancer diagnosis.

EXAMPLE 4

For analyzing the antigens which the monoclonal antibody SLC-454 recognizes, squamous cell lung carcinoma tissue-derived membrane preparations were treated with the enzymes and reagent described below and then examined for the reactivity with SLC-454.

Enzymes and reagent

Trypsin (2.5% solution; product of Gibco)
 0.25% in PBS
Neuraminidase (product of Boehringer Mannheim)
 0.1 U/ml in 0.1M acetate buffer (pH 4.5)-3 mM $CaCl_2$
α-L-Fucosidase (product of Boehringer Mannheim)

0.1 U/ml in 0.1M phosphate buffer (pH 6.3)
Protease (product of Sigma)
10 U/ml in 0.1M phosphate buffer (pH 7.2)
NaIO$_4$ (product of Wako Pure Chemical)
50 mM in PBS The squamous cell lung carcinoma tissue membrane preparations (100 μg of proteins per ml) were distributed, in 50 μl-portions, into the wells of a plate for EIA (product of Linbro). After overnight standing at 4° C., the plate was washed three times with PBS. Then, 1% BSA-PBS was distributed into the wells (200 μl per well). The plate was allowed to stand at room temperature for 30 minutes to 2 hours and then washed three times with PBS. One of the above enzymes and reagent was distributed into the wells (50 μl per well) and the reaction was carried out at 37° C. for 1 hour. Then, the plate was washed five times with PBS and the monoclonal antibody SLC-454 (10 μg/ml) was distributed into the wells (50 μl per well), followed by allowing to stand at 4° C. overnight.

After washing five times with Tween 20 (product of Wako Pure Chemical)-PBS, peroxidase-labeled anti-mouse IgG (400-fold dilution) was added (50 μl per well), and the reaction was carried out at room temperature for 2 hours. The plate was washed five times with Tween 20-PBS, an ABTS substrate solution was added (100 μl), the reaction was conducted for 30 minutes, and the absorbance was measured at 415 nm.

Figure 2:
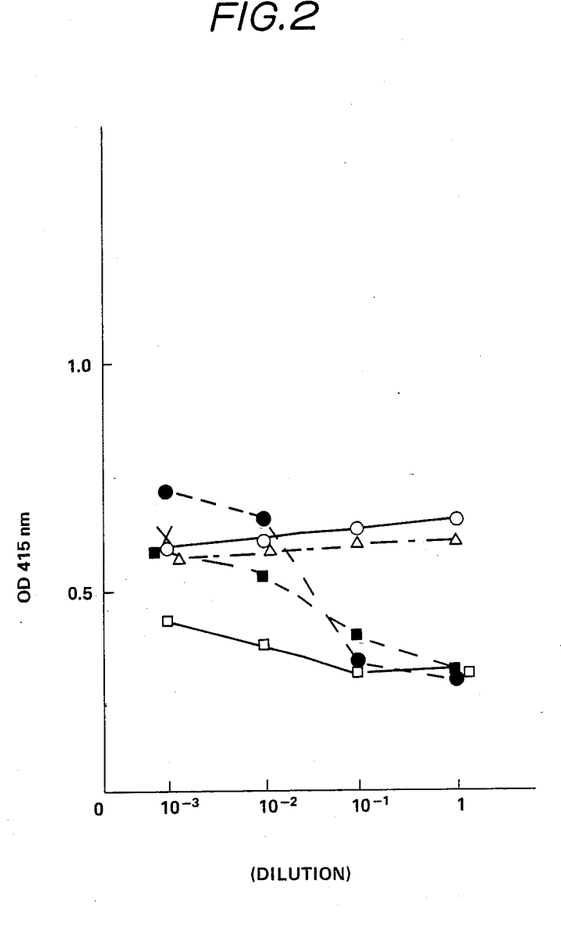
FIG. 2 is a graph showing the results of analysis of the antigens which the monoclonal antibody SLC-454 recognizes.

As shown in FIG. 2, the antigenicity completely disappeared upon treatment with periodate (NaIO$_4$), trypsin or protease. Based on this result, it was estimated that the monoclonal antibody SLC-454 recognizes glycoproteins.

EXAMPLE 5

Pulmonary carcinoma membrane preparations coated on a plate for EIA was blocked by 1% BSA-PBS solution. Serial-dilutions of SLC-454, rabbit anti-CEA antibody, rabbit anti-AFP antibody and rabbit anti-$\beta_2$-microglobulin antibody (all produced by DAKO) were added to the wells. After overnight standing at 4° C., the plate was washed well with PBS. Then, biotin-labeled SLC-454 was added and the plate was allowed to stand at room temperature for 3-4 hours. After washing, avidin-biotin-peroxidase (Vectastain ABC immunoperoxidase staining kit; product of Vector) was added and the plate was allowed to stand at room temperature for 1 hour. Then, an ABTS substrate solution was added and the absorption at 415 nm was measured for each well.

Figure 3:
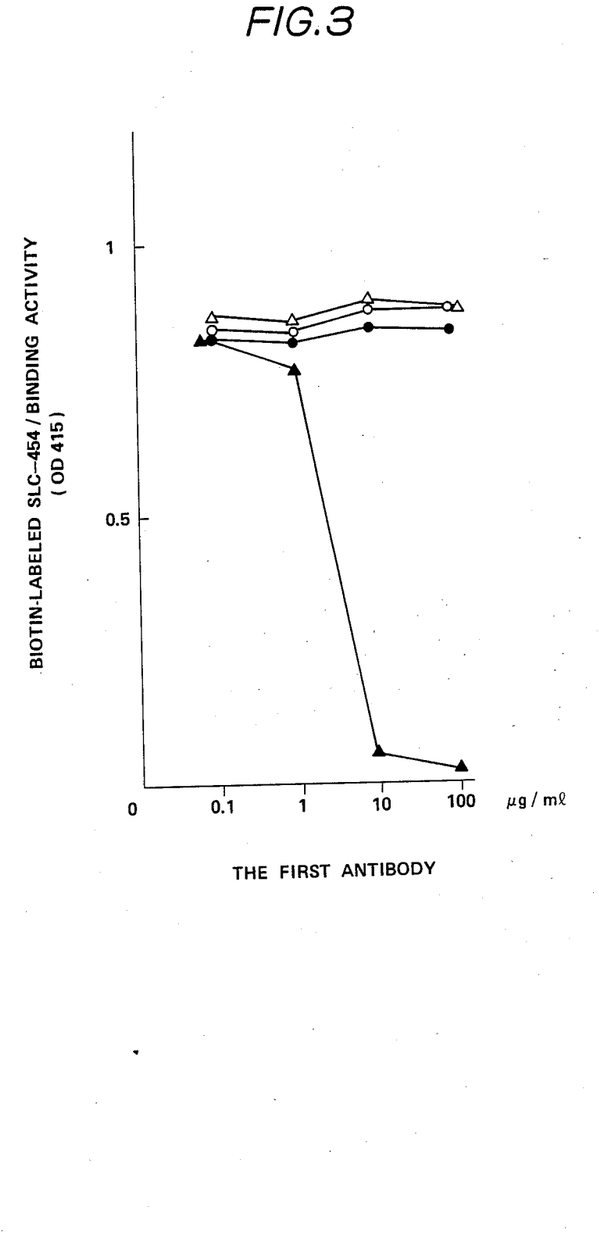
FIG. 3 is a graph showing as to whether or not the binding activity of the monoclonal antibody SLC-454 is inhibited by known tumor markers.

The results are shown in FIG. 3. The binding activity of SLC-454 was inhibited by SLC-454 itself but not at all by anti-CEA antibody, anti-AFP antibody and anti-$\beta_2$ microglobulin. Based on this, it is estimated that SLC-454 recognizes quite different antigens from these antibodies.

While the invention has been described in detail and with reference to specific embodiment thereof, it will be apparent to one skilled in the art that various changes and modifications can be made therein without departing from the spirit and scope thereof.

What is claimed is:

1. An anti-human pulmonary carcinoma antigen specific monoclonal antibody which has the same antigen specificity and binding characteristics as antibodies produced by hybridoma cell line ECACC 86070306, and which belongs to the class IgM, is capable of reacting with human squamous cell lung carcinoma, lung adenocarcinoma and large cell lung carcinoma; is nonreactive with human small cell lung carcinoma and normal human lung cell, and the binding activity of which is substantially unaffected with rabbit anti-$\beta_2$ microglobulin antibody, rabbit anti-CEA antibody and rabbit anti-AFP antibody.

2. The monoclonal antibody according to claim 1, wherein the antibody is identified as SLC-454.

3. The monoclonal antibody according to claim 1, wherein the antibody is produced by cultivated a hybridoma cell line SLC-454 (ECACC 86070306) in a medium or administering the hybridoma to a mouse to thereby cause hybridoma cell propagation in the ascitic fluid in the mouse, followed by separation of the antibody from the culture or ascitic fluid.

* * * * *

UNITED STATES PATENT AND TRADEMARK OFFICE
CERTIFICATE OF CORRECTION

PATENT NO. : 4,892,935
DATED : January 9, 1990
INVENTOR(S) : HAJIME YOSHIDA ET AL.

It is certified that error appears in the above-identified patent and that said Letters Patent is hereby corrected as shown below:

COLUMN 2

Line 14, "protrease," should read --protease,--
Line 51, "antobody-providing" should read --antibody-producing--.
Line 54, "to" should read --to cause--.

COLUMN 10

Line 34, "100 ul" should read --100 µl--.

COLUMN 12

Line 36, "cultivated" should read --cultivating--.

Signed and Sealed this

Twenty-fifth Day of February, 1992

Attest:

HARRY F. MANBECK, JR.

Attesting Officer

Commissioner of Patents and Trademarks